US012721878B2

(12) United States Patent
Sorg et al.

(10) Patent No.: US 12,721,878 B2
(45) Date of Patent: Sep. 1, 2026

(54) POWDERED FOOD SUPPLEMENT FOR PRODUCING A BEVERAGE

(71) Applicant: PM-INTERNATIONAL AG, Schengen (LU)

(72) Inventors: Rolf Sorg, Schengen (LU); Tobias Kühne, Morbach (DE); Wilhelm Messer, Bad Dürkheim (DE)

(73) Assignee: PM-INTERNATIONAL AG, Schengen (LU)

( * ) Notice: Subject to any disclaimer, the term of this patent is extended or adjusted under 35 U.S.C. 154(b) by 289 days.

(21) Appl. No.: 18/273,947

(22) PCT Filed: Feb. 15, 2022

(86) PCT No.: PCT/EP2022/053669
§ 371 (c)(1),
(2) Date: Jul. 24, 2023

(87) PCT Pub. No.: WO2022/179889
PCT Pub. Date: Sep. 1, 2022

(65) Prior Publication Data

US 2024/0307476 A1 Sep. 19, 2024

(30) Foreign Application Priority Data

Feb. 23, 2021 (DE) ..................... 10 2021 104 285.2

(51) Int. Cl.

| | |
|---|---|
| ***A61K 36/73*** | (2006.01) |
| ***A23L 2/39*** | (2006.01) |
| ***A23L 2/56*** | (2006.01) |
| ***A23L 2/60*** | (2006.01) |
| ***A23L 2/68*** | (2006.01) |
| ***A61K 9/00*** | (2006.01) |
| ***A61K 31/197*** | (2006.01) |
| ***A61K 31/4188*** | (2006.01) |
| ***A61K 31/4415*** | (2006.01) |
| ***A61K 31/455*** | (2006.01) |
| ***A61K 31/51*** | (2006.01) |
| ***A61K 31/525*** | (2006.01) |
| ***A61K 31/714*** | (2006.01) |
| ***A61K 33/30*** | (2006.01) |
| ***A61K 36/258*** | (2006.01) |
| ***A61K 36/87*** | (2006.01) |
| ***A61K 36/88*** | (2006.01) |
| ***A61K 36/906*** | (2006.01) |
| ***A61K 47/12*** | (2006.01) |
| ***A61K 47/26*** | (2006.01) |

(52) U.S. Cl.
CPC ................ *A61K 36/73* (2013.01); *A23L 2/39* (2013.01); *A23L 2/56* (2013.01); *A23L 2/60* (2013.01); *A23L 2/68* (2013.01); *A61K 9/0095* (2013.01); *A61K 31/197* (2013.01); *A61K 31/4188* (2013.01); *A61K 31/4415* (2013.01); *A61K 31/455* (2013.01); *A61K 31/51* (2013.01); *A61K 31/525* (2013.01); *A61K 31/714* (2013.01); *A61K 33/30* (2013.01); *A61K 36/258* (2013.01); *A61K 36/87* (2013.01); *A61K 36/88* (2013.01); *A61K 36/906* (2013.01); *A61K 47/12* (2013.01); *A61K 47/26* (2013.01)

(58) Field of Classification Search
None
See application file for complete search history.

(56) References Cited

FOREIGN PATENT DOCUMENTS

| | | | | |
|---|---|---|---|---|
| EP | 1637149 A1 | | 3/2006 | |
| WO | WO-2007089652 A2 | * | 8/2007 | .......... A61K 9/0058 |

OTHER PUBLICATIONS

Anonymous: "PM International English—ELAB Analytik GmbH, Men+", Jun. 23, 2020 (Jun. 23, 2020), pp. 1-7, XP093216276, retrieved from the internet: URL:https://elab-analytik.de/pm-international-english/.

Dittrich Tino: "CHEERS—Prostate Formula, 60 Capsules for Urinary and Prostate Support, Prostate Supplement for Men, Selenium Supplement with Vitamin B6 and Zinc: Amazon.de: Health & Personal Care", Aug. 7, 2020 (Aug. 7, 2020), XP093216261, retrieved from the internet: URL:https://www.amazon.de/CHEERS-Prostata-Formel-ProstataUnterstutzung-Prostata-Erganzmittel-Selen-Erganzmittel/dp/B07WF8PG9T?ref_=ast_sto_dp.

Anonymous: "81 c5rv1 mZCL.jpg (1632x1224), CHEERS—Prostate Formula, 60 Capsules for Urinary and Prostate Support, Prostate Supplement for Men, Selenium Supplement with Vitamin B6 and Zinc: Amazon.de: Health & Personal Care", Aug. 7, 2020 (Aug. 7, 2020), XP093216262, retrieved from the internet: URL:https://m.media-amazon.com/images/I/81 c5rv1 mZCL.jpg.

Database GNPD [Online] MINT; Jun. 3, 2020 (Jun. 3, 2020), anonymous: "BlueBoost Complex Capsules", XP093216268, Database accession No. 7666105.

Anonymous: "Publication date of document D2", Feb. 19, 2021 (Feb. 19, 2021), XP093216312.

First Examination Report, corresponding to EP4297588, dated Oct. 24, 2024.

Pm-International: "Fitline Men+ Launch Video 2021", Feb. 22, 2021 (Feb. 22, 2021), XP55931014, retrieved from the Internet: URL:https://vimeo.com/515217953 [retrieved on Jun. 8, 2022].

Anonymous: "Fitline MEN+", Jun. 7, 2022 (Jun. 7, 2022), pp. 1-1, XP055928697, retrieved from the Internet: URL: https://www.pmebusiness.com/files/my/product_usage/FL.Men+Can.LMIV.LBLS.0521.MY.P4_INTERNET.pdf [retrieved on Jun. 8, 2022].

(Continued)

*Primary Examiner* — Michael V Meller
(74) *Attorney, Agent, or Firm* — Quarles & Brady LLP

(57) ABSTRACT

A powdered dietary supplement, containing a) 50 to 90% by weight of at least one saccharide, b) 2 to 20% by weight of apple extract, wine grape extract and saffron, c) at least one herbal extract selected from ginger extract, *ginseng* extract and pepper extract, d) at least one zinc compound, e) at least two B group vitamins, and f) at least one acidifying agent.

10 Claims, No Drawings

(56) References Cited

OTHER PUBLICATIONS

Anonymous: "Enostim: the new solution for men's health", May 18, 2015 (May 18, 2015), XP055931047, retrieved from the Internet: URL:https://nutraceuticalbusinessreview.com/news/article_page/Enostim_the_new_solution_for_mens_health/108487 [retrieved on Jun. 14, 2022].

Anonymous: "Sex and the Supplement: Dietary Supplement Ingredients for Male Sexual Health", Oct. 27, 2017 (Oct. 27, 2017), XP055931057, retrieved from the Internet: URL:https://www. nutritional outlook. com/view/sex-and-supplement-dietarysupplement-ingredients-male-sexual-health [retrieved on Jun. 14, 2022].

Kim Young-Chan et al: "Effect of Korean Red Ginseng on Sexual Dysfunction and Serum Lipid Level In Old Aged Men", Journal of Ginseng Research, Go'ryeo Insam Haghoe, Seoul, KR, Bd. 20, Nr. 2, Aug. 30, 1996 (Aug. 30, 1996), pp. 125-132, XP053007984,ISSN: 1226-8453.

International Search Report and Written Opinion, corresponding to PCT/EP2022/053669, dated Jun. 23, 2022.

* cited by examiner

POWDERED FOOD SUPPLEMENT FOR PRODUCING A BEVERAGE

CROSS-REFERENCE TO RELATED APPLICATIONS

The present application is a national stage application filed under 35 U.S.C. § 371 of International Application No. PCT/EP2022/053669, filed Feb. 15, 2022, which claims priority to German Patent Application No. 10 2021 104 285.2, filed Feb. 23, 2021. Each of the aforementioned patent applications is incorporated herein by reference in its entirety for all purposes.

DESCRIPTION

The disclosure relates to a powdered dietary supplement from which a liquid administration form can be obtained by adding water.

Dietary supplements are often offered as capsules. Capsules are usually swallowed with water. Dietary supplements offered as powders are usually mixed with water by the user to obtain a liquid administration form that is drinkable. This is advantageous compared to the presentation as capsules in order to improve the absorption of valuable ingredients in the gastrointestinal space, to simplify the intake of the dietary supplement and to avoid complications during ingestion.

In the case of powdered dietary supplements, however, the dissolution behavior of the ingredients and/or the taste of the liquid obtained is a problem in many cases. Also unsatisfactory with many dietary supplements is the insufficient bioavailability of valuable ingredients.

In one field of application, dietary supplements are generally intended to support the sexual performance of men. A further improvement of the support would be desirable. In addition, in this field, dietary supplements are generally offered as capsules, as ingredients used often do not have a pleasant taste (bitter taste).

The object is therefore to provide a powdered dietary supplement that can be suitable for supporting male sexual performance and that dissolves as quickly and extensively as possible in water to provide a drinkable administration form with a good taste, which at the same time enables high bioavailability of the ingredients, which can further promote the desired support.

The object is solved according to the disclosure by the dietary supplement and the method for preparing a beverage as well as the obtained beverage according to the independent claims. Preferred embodiments are mentioned in the dependent claims.

The disclosure thus relates to a powdered dietary supplement, containing (a) 50 to 90% by weight of at least one saccharide,
(b) 2 to 20% by weight of apple extract, grape extract and saffron,
(c) at least one herbal extract selected from ginger extract, *ginseng* extract and pepper extract,
d) at least one zinc compound,
e) at least two B group vitamins and
f) at least one acidifying agent.

The dietary supplement according to the disclosure is in the form of a powder. In particular, it is not a dietary supplement in the form of a capsule, i.e. the dietary supplement in powder form is not encapsulated. A particular advantage of the powdered dietary supplement according to the disclosure is that it dissolves to a large extent in water, so that a liquid administration form or beverage for oral intake can be provided by adding water. After dissolution in water, a proportion of small particles may still be detectable floating up, which is due to contained polyphenols. Significant sedimentation is not observed even after letting the beverage stand for some time.

The obtained beverage has a good taste. An administration form as a capsule, which is common due to the unpleasant taste of prior art formulations, is not required.

The dietary supplement according to the disclosure may show better bioavailability of the ingredients, which, together with the specific combination of ingredients, may lead to an improved result in terms of supporting sexual performance in men.

The powdered dietary supplement according to the invention disclosure contains 50 to 90% by weight, preferably 70 to 85% by weight, of at least one saccharide, based on the total weight of the dietary supplement, wherein the at least one saccharide is preferably at least one monosaccharide, in particular fructose and/or dextrose, particularly preferably dextrose.

The dietary supplement has a high proportion of saccharide, which is advantageous for good taste, especially when at least one monosaccharide is used, preferably fructose or especially dextrose. Saccharides, in particular monosaccharides themselves, are readily soluble in water. Thus, monosaccharides in particular, preferably dextrose and/or fructose, dissolve very rapidly in water and impart a pleasant taste to the liquid obtained in combination with the other ingredients. Furthermore, dextrose improves the absorption of certain ingredients.

The powdered dietary supplement according to the disclosure contains a combination of apple extract, wine grape extract or grape extract and saffron. The apple extract is an extract from the apple (*Malus*, in particular *Malus domestica*, e.g. *Malus pumila*), preferably an extract from the apple fruit, in particular from peels of the apple fruit. Wine grape extract is an extract from grapes (*Vitis vinifera*), preferably an extract from grape pomace (grape pomace extract). Both apple extract and wine grape extract are characterized by a high content of polyphenols. Thus, the apple extract and the wine grape extract or grape pomace extract may have a polyphenol content of more than 40% by weight, preferably more than 50% by weight, of polyphenols, e.g., 45 to 90% by weight, based on the total weight of apple extract and wine grape extract contained in the dietary supplement. In particular, the saffron (*Crocus sativus*) is saffron powder. Saffron or saffron powder is a well-known spice usually obtained from the stigmas of saffron flowers. The effect of saffron as an aphrodisiac is known since ancient times.

The respective proportions of apple extract, wine grape extract and saffron contained in the dietary supplement, based on the total weight of apple extract, wine grape extract and saffron, are preferably as follows:

40 to 85% by weight, preferably 50 to 75% by weight, of wine grape extract,
12 to 45% by weight, preferably 18 to 40% by weight, of apple extract and
2 to 22% by weight, preferably 4 to 18% by weight, of saffron.

Studies have proven the positive effect of a combination of apple extract, wine grape extract and saffron on sexual performance in men. Studies by commodity manufacturers, for example, have shown that such a combination activates eNOs (endothelial nitric oxide synthase), which can increase blood flow by up to 50%. The nitric oxide (NO) pathway is essential to the blood flow mechanism that enables penile erection. The sNOs synthesizes NO and is thus directly related to blood flow.

In addition, in a 4-week study with men over 45 years of age, the effect of daily use of such a combination was evaluated using the so-called Erection Hardness Scale (EHS). More than 70% of the test persons showed an increase in the EHS.

The term extract or herbal extract refers here, as is generally customary, to a dried extract (dry extract) from corresponding plants or parts of plants, with the extract being obtained in particular with the aid of an organic solvent, preferably an alcohol, in particular ethanol, and/or water as extraction agent and with a drug-extract ratio of between 120:1 and 10:1. The calculation of the drug extract ratio (DER) for extracts is known to the person skilled in the art. The plants or parts of plants are thereby referred to as drugs.

The powdered dietary supplement according to the disclosure further comprises at least one herbal extract selected from ginger extract, *ginseng* extract and pepper extract. These extracts have been shown to increase the bioavailability of the ingredients, such as active ingredients, vitamins and nutrients, of the dietary supplement, even at low dosages, and thus can increase the efficacy (bioenhancer). Bioavailability is a pharmacological measure of the proportion of an ingredient that is available unchanged in the systemic circulation (especially in the bloodstream).

The ginger extract is an extract of ginger (*Zingiber officinale*), preferably an extract of the rhizome of ginger (*Zingiberis rhizoma*). The *ginseng* extract is an extract of *ginseng* (*Panax ginseng*), preferably an extract of red *ginseng*, with the extract preferably containing at least 5% by weight of ginsenosides. *Ginseng* or red *ginseng* generally refers to the *ginseng* root. The pepper extract is an extract of pepper, preferably black pepper (*Piper nigrum*).

The powdered dietary supplement according to the disclosure preferably contains two or all three herbal extracts selected from ginger extract, *ginseng* extract and pepper extract. Thus, ginger extract and *ginseng* extract or ginger extract and pepper extract or *ginseng* extract and pepper extract or ginger extract and *ginseng* extract and pepper extract, as described above including the preferred embodiments, are preferably used as the herbal extract according to component c).

In a preferred embodiment, the dietary supplement according to the disclosure contains the *ginseng* extract, in particular the red *ginseng* extract, preferably with at least 5% by weight of ginsenosides, alone or in combination with one or both of ginger extract and pepper extract.

In addition to improving bioavailability, *ginseng* extract also provides additional support for sexual performance and in this sense acts synergistically with the combination of apple extract, wine grape extract and saffron. The use of *ginseng* as a natural aphrodisiac was already known in traditional Chinese medicine. The *ginseng* extract thus has a dual function.

The herbal extracts selected from ginger extract, *ginseng* extract, and pepper extract in the food product, if used, are preferably used in the following amounts based on 100 g of the powdered dietary supplement:

- 3 mg to 200 mg, preferably 5 mg to 50 mg, of pepper extract,
- 3 mg to 200 mg, preferably 5 mg to 50 mg, of ginger extract,
- 200 mg to 5 g, preferably 250 mg to 3 g, of *ginseng* extract.

The powdered dietary supplement according to the disclosure further comprises at least two B group vitamins. The at least two B group vitamins are preferably selected from one or more of the group consisting of

- pantothenic acid (vitamin B5) or a salt thereof,
- pyridoxine (vitamin B6) or a salt thereof,
- thiamine (vitamin B1) or a salt thereof,
- riboflavin (vitamin B2) or a salt thereof,
- cyanocobolamine (vitamin B12) or a salt thereof,
- biotin (vitamin B7) or a salt thereof,
- niacin (vitamin B3) or a salt thereof, preferably containing at least three, more preferably at least five, or all of said B group vitamins.

In a preferred embodiment, the vitamins B2, B3, B5, B6, B7, and B12, or more preferably the vitamins B1, B2, B3, B5, B6, B7, and B12, are contained in the dietary supplement of the disclosure.

A suitable salt of pantothenic acid is e.g. calcium pantothenate. A suitable salt of pyridoxine is e.g. pyridoxine hydrochloride. A suitable salt of thiamine is e.g. thiamine hydrochloride.

The total amount of two or more B group vitamins dietary supplement, preferably the above six or seven B group vitamins, is preferably in a range of 50 mg to 1,000 mg, more preferably 100 mg to 500 mg, based on 100 g of the powdered dietary supplement. Even if a salt of the vitamin is used, only the vitamin itself is taken into account. This also applies to the following information.

Appropriate proportions of B group vitamins, if used and based on 100 g of the powdered dietary supplement, are as follows:

- 20 mg to 270 mg of pantothenic acid,
- 5 mg to 100 mg of pyridoxine,
- 5 mg to 70 mg of thiamine,
- 4 mg to 70 mg of riboflavin,
- 10 μg to 10 mg of cyanocobolamine,
- 0.2 mg to 7 mg of biotin,
- 80 mg to 1500 mg of niacin.

The powdered dietary supplement according to the disclosure further comprises at least one zinc compound. The zinc compound serves to provide zinc, which belongs to the essential trace elements. Suitable zinc compounds include, for example, inorganic zinc salts or zinc complexes with organic acids and amino acids. Specific examples are zinc sulfate, zinc glycinate, zinc gluconate, zinc histidine and zinc aspartate, with zinc gluconate being preferred.

The amount of the at least one zinc compound is preferably selected such that the content of zinc, based on 100 g of the powdered dietary supplement, is in the range of 25 mg to 250 mg, preferably 50 mg to 150 mg.

The powdered dietary supplement according to the disclosure further comprises at least one acidifying agent, preferably citric acid. The at least one acidifying agent, preferably citric acid, is preferably present in an amount of from 4% to 10% by weight, based on the total weight of the powdered dietary supplement.

Citric acid is also beneficial because it can increase the bioavailability of the ingredients of the dietary supplement. Furthermore, citric acid may also be useful for improving the taste of the dietary supplement, e.g. due to its intrinsic taste and by masking a bitter taste, especially in combination with sweeteners. Citric acid also exhibits preservative properties.

The powdered dietary supplement according to one of the preceding claims may further comprise g) one or more flavoring agents, in particular natural flavoring agents, and/or h) one or more sweeteners, in particular steviolgylcosides.

The flavoring agents and sweeteners serve in particular to improve the taste of the dietary supplement or to mask an unpleasant taste, in particular a bitter taste, which may originate in particular from the herbal extracts.

In a preferred embodiment, a combination of at least one flavoring agent for suitable flavoring, e.g., fruit flavoring, is used in combination with at least one flavoring agent for masking (flavor masking agent). An example is the selection of a fruit flavoring with masking cherry flavor and masking with a bitter masker flavoring (bitter flavor masking agent, e.g., Resolver® from Wild, e.g., specification Art. No. 38170605550000).

The flavoring agent or agents, in particular natural flavoring agents, may serve to impart a particular flavor to the dietary supplement, e.g. a fruit flavor, such as cherry flavor. Such flavoring agents are known to the person skilled in the art.

Steviolgylcosides are particularly suitable sweeteners. As already mentioned above, a combination of sweetener and citric acid can result in an enhanced taste-masking effect, particularly with regard to a bitter taste.

The powdered dietary supplement may contain further additives customary in the field, e.g. one or more coloring agents that impart a desired color to the powdered dietary supplement or to the beverage that can be prepared therefrom. The addition of further herbal extracts or herbal concentrates is also conceivable.

In a preferred embodiment, the powdered dietary supplement contains (a) 50 to 90% by weight, preferably 70 to 85% by weight, of at least one monosaccharide, preferably dextrose and/or fructose, b) 2 to 20% by weight of apple extract, wine grape extract and saffron, c) at least one, two or preferably three herbal extracts selected from ginger extract, *ginseng* extract and pepper extract, wherein the *ginseng* extract is preferably a red *ginseng* extract and the pepper extract is preferably a black pepper extract, d) at least one zinc compound, e.g. zinc gluconate, e) at least three, preferably at least five, B group vitamins selected from pantothenic acid or a salt thereof, pyridoxine or a salt thereof, thiamine or a salt thereof, riboflavin or a salt thereof, cyanocobolamine or a salt thereof, biotin or a salt thereof, and niacin or a salt thereof, in particular vitamins B2, B3, B5, B6, B7 and B12 or vitamins B1, B2, B3, B5, B6, B7 and B12, f) 4% by weight to 10% by weight of citric acid as an acidifying agent and g) one or more flavoring agents, preferably natural flavoring agents, and h) one or more sweeteners, in particular steviolglycosides, and i) optionally, one or more colorants, wherein the proportions of components b), c), d) and e) are preferably as indicated above.

The powdered dietary supplement according to the disclosure is characterized by a combination of ingredients which, on the one hand, can be dissolved well and quickly in water to obtain a liquid administration form with a pleasant taste. On the other hand, the combination of ingredients causes a synergistic interaction, which can lead to improved support for male sexual performance.

The powdered dietary supplement according to the disclosure, or consumption of the aqueous liquid administration form that can be prepared therewith, may therefore be suitable for supporting a man's sexual performance or be of use in cases of erectile dysfunction, e.g., for prevention and for supporting erectile hardness by promoting blood flow and self-confidence (B vitamins), as well as hormonal activity (testosterone production by zinc and *ginseng* and B vitamin). It is understood that the liquid administration form or drink is administered by drinking.

The effects of the combination of apple extract, wine grape extract, and saffron on male sexual performance, as well as the increase in bioavailability through the use of ginger extract, *ginseng* extract, and/or pepper extract, have been discussed above. Advantageous properties of further ingredients and synergistic effects, which may be based on contained groups of ingredients or groups of ingredients in preferred embodiments, are given below.

The combination of apple extract, wine grape extract and saffron in conjunction with the preferred *ginseng* extract leads to another synergistic effect that can provide improved sexual performance support.

Studies have shown that the synergy group apple extract, grapes and saffron+zinc+vitamins B2, B3, B6, B12 leads to higher NO production in the body, which may result in better blood flow to the erectile tissue and a better, faster, longer and/or more frequent erection. It is well known that penile erection is mediated by nitric oxide (NO). Riboflavin, pyridoxine and vitamin B12 contribute to the maintenance of normal red blood cells. In addition, zinc plays a role in cell division.

Another aspect is the strengthening of self-confidence. It is generally known that the psyche plays a major role in erectile dysfunction, especially fear of failure. This often leads to a vicious circle after a single failure (self-fulfilling prophecy). A suitable synergy group to support the psyche is zinc+vitamins B3, B5, B6, B7, B12+*ginseng* extract, although the individual components can also be effective on their own. Vitamins B3, B5, B6, B7, B12 support normal psychological and mental functions.

Another aspect may be timely prevention, for example before erectile dysfunction develops. An important cause is a decline in testosterone production in men of advanced age. A suitable synergy group for this is zinc+*ginseng*+vitamin B5, B6, although the individual components can also be effective on their own. Thus, vitamin B5 contributes to the normal synthesis and metabolism of steroid hormones. Vitamin B6 contributes to the regulation of hormone activity. Zinc supports the maintenance of normal testosterone levels in the blood. Zinc also contributes to normal fertility and reproduction.

The disclosure also relates to a method for the preparation of a beverage comprising the addition of water to the powdered dietary supplement of the disclosure as described above to obtain a liquid administration form, wherein the dissolving process may optionally be assisted by stirring, for example with a spoon. Suitably, the powder of the dietary supplement is stirred in water, preferably cold water (i.e., not heated water), until it is substantially dissolved to obtain the finished beverage. Advantageously, when the drink is consumed, the ingredients from the solution can enter the bloodstream particularly quickly.

An appropriate amount for a serving or beverage is about 3 g to 7 g of the powdered dietary supplement stirred into about 100 ml to 250 ml of water or cold water until the powder is substantially dissolved to obtain a liquid administration form.

An exemplary dosage is, for example, dissolving about 5 g of the powdered dietary supplement in about 150 ml of water to obtain one serving or drink. A recommended dosage is the consumption of one or two drinks prepared in this way per day.

It has been shown that the powdered dietary supplement dissolves readily and rapidly in water at room temperature (e.g., 23° C.) and in the amounts specified. By merely adding water to the powdered composition in a drinking vessel and stirring briefly, a drinkable liquid can be prepared at room temperature. The ingredients are largely dissolved or at least stably suspended, and floating particles may also be present. Even after allowing the prepared beverage to stand for a certain time (e.g. 1 minute), no or at most slight sedimentation is observed.

The disclosure also relates to a beverage consisting of or comprising water and the powdered dietary supplement of the disclosure as described above, preferably an amount of about 3 g to 7 g of the powdered dietary supplement mixed in about 100 ml to 250 ml of water. As discussed above, the dietary supplement generally dissolves substantially or at least becomes suspended, and particles may be present that float. Even after allowing the beverage to stand for a period of time (e.g., 1 minute) after preparation, no or at most minor sedimentation is observed. It is understood that the beverage can be produced by the method according to the disclosure.

Embodiments and features of the disclosure described above may be combined with each other, as long as the context does not indicate otherwise. The disclosure is further described below by means of an example, which is for illustrative purposes only and is not intended to limit the disclosure in any way.

EXAMPLES

Example 1

A powdered dietary supplement was formulated that included the following ingredients, based on 100 g of the powder:

| Ingredient | Quantity per 100 g |
|---|---|
| Dextrose | 78 g |
| Acidifier: citric acid | 8.6 g |
| Apple extract, wine grape extract and saffron powder | 7.5 g |
| Natural flavoring agents | 1.9 g |
| Color: beta-carotene (1% by weight on carrier) | 1.5 g |
| Red ginseng extract (55-60% by weight maltodextrin, 40-45% by weight red ginseng extract). | 1.1 g |
| Zinc gluconate | 0.75 g |
| Sweetener: steviolglycosides (steviolglycosides, flavor) | 0.32 g |
| Nicotinamide (niacin [niacin equivalent]) | 0.15 g |
| Calcium D-pantothenate (pantothenic acid) (=60 mg pantothenic acid) | 65 mg |
| Ginger extract powder | 27 mg |
| Pyridoxine hydrochloride (vitamin B6) (=14 mg vitamin B6) | 17 mg |
| Thiamine hydrochloride (vitamin B1) (=11 mg vitamin B1) | 14 mg |
| Riboflavin (vitamin B2) | 11 mg |
| Cyanocobalamin (0.1% by weight on carrier) (vitamin B12) (=25 μg vitamin B12) | 25 mg |
| D-Biotin | 500 μg |

Based on the total weight of apple extract, wine grape extract and saffron powder, the proportions are about 60-65% wine grape extract, about 25-30% apple extract and about 8-12% saffron powder. The aroma substances contain cherry aroma.

5 g of the obtained powder is stirred with a spoon into 150 ml of cold water. The powder dissolves quickly and largely in the water, obtaining a drinkable liquid. No significant sedimentation is observed. The liquid obtained had a pleasant taste of cherries. Thus, a pleasant tasting beverage is provided for consumption. Recommended is 1 to 2 such servings daily.

Example 2

An efficacy study was conducted with the powdered dietary supplement according to Example 1 above with the following general conditions.

Recruitment

The recruitment criteria were as follows:

- Age≥40 years
- Interested in sexual activities
- Self-perceived loss of erectile hardness, first noticed at age greater than 40 years
- Desire to participate in the study and willing to provide information about sexual function
- No potential health risks from participation in the study
- No contraindicating use of medications or supplements that may affect erection hardness, such as.
  - Cardiac drugs (nitrates)
  - Medication for urinary symptoms (alpha blockers)
  - medicines for cardiac arrhythmias (beta blockers)
  - Insulin therapy
  - Therapy with antidepressants
  - Therapy with vasodilator
  - Or other ongoing treatment for erectile dysfunction.
- No smokers
- No alcohol consumption A total of 38 men from Hong Kong, Malaysia, Taiwan, Japan, and South Korea met the recruitment criteria and participated in our study.

Protocol

Participants were asked to continue their normal food intake and exercise program throughout the study period.

At the start of the study, all participants were asked not to take any nonessential medications or supplements that might affect erection hardness for 2 weeks. They were asked to monitor their physical condition during the 2-week washout period, which formed the baseline for subjective comparison after supplementation.

During the washout period, participants were each assigned two doses of the powdered dietary supplement according to Example 1. They were instructed to begin taking the dietary supplement after the two-week washout period. The recommended dosage was 5 grams in 150 ml of water per serving. The instructions for use were to take once in the morning and once in the evening. At this dosage, the amount of the allotted product was enough for 30 days.

After 3 weeks of product use, participants were asked to complete an online survey that included the following questions. They were asked to provide their subjective responses, referring to how they felt during the 2-week washout period.

The evaluation criteria used are as follows:

5 (strongly agree)
4 (agree)
3 (neutral)
2 (do not agree)
1 (do not agree at all)

Survey Questions:

1. The product is effective
2. My mood improved after using the product
3. I had more energy after using the product
4. I was more awake after using the product
5. I was more active after using the product 6. I had a stronger sexual libido after using the product
7. I became hard more often after using the product
8. My speed to get hard was faster after using the product
9. My hardness has improved after using the product
10. I am more confident that I can achieve hardness after using the product
11. I am more confident that I can maintain hardness after using the product
12. I feel younger after using the product
13. The product allows me sexual intimacy whenever I feel like it
14. The product tastes good Participants were informed about all study procedures in their local language. They were contacted by telephone at the beginning of the supplementation period (after the 2-week washout period) and 3 days before the online survey. The survey was administered after 2 weeks of washout+3 weeks of supplementation. These telephone calls were used to obtain verbal confirmations of compliance with the study protocol.

Results

More than 60% of men agreed that they had better erection hardness and stronger sexual libido, and they were more confident in achieving and maintaining hardness after using the product for 3 weeks.

Participants were also more active, with just over 58% reporting that they were more alert, had a faster erection and were hard more often after using the product.

Detailed breakdowns of the results are shown below:

| | Answers total | 5* | 4* | 3* | 2* | 1* | Consent total | Consent Percentage |
|---|---|---|---|---|---|---|---|---|
| I was more active after using the product | 36 | 9 | 15 | 9 | 1 | 2 | 24 | 66.7 |
| I am more confident that I can achieve hardness after using the product | 36 | 8 | 15 | 8 | 3 | 2 | 23 | 63.9 |
| The product tastes good | 36 | 6 | 16 | 11 | 1 | 2 | 22 | 61.1 |
| I had a stronger sexual libido after using the product | 36 | 7 | 15 | 8 | 4 | 2 | 22 | 61.1 |
| My hardness has improved after using the product | 36 | 9 | 13 | 9 | 3 | 2 | 22 | 61.1 |
| I am more confident that I can maintain the hardness after using the product | 36 | 7 | 15 | 9 | 3 | 2 | 22 | 61.1 |
| I had more energy after using the product | 36 | 12 | 9 | 11 | 2 | 2 | 21 | 58.3 |
| I was more awake after using the product | 36 | 8 | 13 | 10 | 3 | 2 | 21 | 58.3 |
| I became hard more often after using the product | 36 | 11 | 10 | 10 | 3 | 2 | 21 | 58.3 |
| My speed to get hard was faster after using the product | 36 | 6 | 15 | 10 | 3 | 2 | 21 | 58.3 |
| The product is effective | 36 | 9 | 11 | 13 | 1 | 2 | 20 | 55.6 |
| I had a stronger desire for sexual intimacy after using the product | 36 | 6 | 14 | 10 | 4 | 2 | 20 | 55.6 |
| I feel younger after using the product | 36 | 8 | 9 | 15 | 2 | 2 | 17 | 47.2 |

*5 = strongly agree, 4 = agree, 3 = neutral, 2 = disagree, 1 = disagree at all.

The invention claimed is:

1. A powdered dietary supplement, consisting essentially of:

a) 50% to 90% by weight of dextrose;

b) 2% to 20% by weight of a mixture of apple extract, wine grape extract and saffron;

c) ginger extract and red *ginseng* extract;

d) zinc gluconate;

e) a mixture of B vitamins consisting essentially of Pyridoxine hydrochloride (vitamin B6), Thiamine hydrochloride (vitamin B1), Riboflavin (vitamin B2), Cyanocobalamin (vitamin B12), Nicotinamide (vitamin B3), D-Biotin (vitamin B7), and Calcium D-pantothenate (pantothenic acid (vitamin B5));

f) citric acid;

g) steviol glycoside; and h) beta-carotene.

2. The powdered dietary supplement of claim 1, consisting essentially of 3 mg to 200 mg of ginger extract and 200 mg to 5 g of red *ginseng* extract.

3. The powdered dietary supplement of claim 1, consisting essentially of 40% to 85% by weight of wine grape extract, 12% to 45% by weight of apple extract and 2% to 22% by weight of saffron.

4. The powdered dietary supplement of claim 1, wherein the mixture of B vitamins is present in a total amount ranging from 50 mg to 1,000 mg based on 100 g of the powdered dietary supplement.

5. The powdered dietary supplement of claim 1, wherein the amount of the zinc gluconate is in the range of 25 mg to 250 mg.

6. The powdered dietary supplement of claim 1, wherein the citric acid is present in an amount of from 4% to 10% by weight.

7. The powdered dietary supplement of claim 1, consisting essentially of 4% by weight to 10% by weight citric acid.

8. The powdered dietary supplement of claim 7, which, based on 100 g of the powdered dietary supplement, consists essentially of 3 mg to 200 mg of ginger extract, 200 mg to 5 g of red *ginseng* extract, 40 to 85% by weight of wine grape extract, 12 to 45% by weight of apple extract, 2 to 22% by weight of saffron, the mixture of the B vitamins ranging from 50 mg to 1,000 mg based on 100 g of the powdered dietary supplement, and zinc gluconate in a range of 25 mg to 250 mg.

9. A method for the preparation of a beverage consisting essentially of the addition of water to the powdered dietary supplement of claim 1 to obtain a liquid administration form, wherein an amount of 3 g to 7 g of the powdered dietary supplement is added to 100 ml to 250 ml of water to obtain a serving.

10. A beverage consisting essentially of water and the powdered dietary supplement of claim 1, wherein an amount of 3 g to 7 g of the powdered dietary supplement is mixed in 100 ml to 250 ml of water.

* * * * *